United States Patent [19]

Nevins et al.

[11] Patent Number: 4,954,447

[45] Date of Patent: Sep. 4, 1990

[54] FERAXANASE, A HIGHLY SPECIFIC ENZYME FOR HYDROLYSIS OF COMPLEX POLYSACCHARIDES

[75] Inventors: Donald J. Nevins, Davis, Calif.; Kazuhiko Nishitani, Kagoshima, Japan

[73] Assignee: The Regents of the University of California, Oakland, Calif.

[21] Appl. No.: 223,125

[22] Filed: Jul. 22, 1988

[51] Int. Cl.$^5$ .................... C12N 15/56; C12N 9/24

[52] U.S. Cl. ..................... 435/200; 435/71.1; 435/839; 435/832

[58] Field of Search .............. 435/200, 201, 202, 205, 435/209, 839, 68, 71.1

[56] References Cited

U.S. PATENT DOCUMENTS 4,742,005  5/1988  Yamanobe et al. ............... 435/200

OTHER PUBLICATIONS

Dubois et al., "Colorimetric Method for Determination of Sugars and Related Substances," *Anal. Chem.*, 28:350–356, (1956).

Talmadge et al., "The Structure of Plant Cell Walls I.," *Plant Physiol.*, 51:158–173, (1973).

Huber and Nevins, "Preparation and Properties of a β-D-Glucans . . . ," *Plant Physiol.*, 60:300–304, (1977).

Wilkie, "The Hemicellulose of Grasses and Cereals," *Adv. Carbohydr. Chem. Biochem.*, 36:215–264, (1979).

Darvill et al., "Structure of Plant Cell Walls, XI Glucuronoarabinoxylan, a Second Hemicellulose in the Primary Cell Walls of Suspension-Cultured Sycamore Cells," *Plant Physiol.*, 66:1135–1139, (1980).

Yamamoto et al., "Effects of Auxin on the Structure of Hemicellulose of Avena Coleoptiles," *Plant Cell Physiol.*, 21:373–381, (1980).

Carpita, N.C., "Hemicellulosic Polymers of Cell Walls of Zea Coleoptiles," *Plant Physiol.*, 72:515–521, (1983).

Carpita, "Cell Wall Development in Maize Coleoptiles," *Plant Physiol.*, 76:205–212, (1984).

Kato and Nevins, "Enzymic Dissociation of Zea Shoot Cell Wall Polysaccharides, III," *Plant Physiol.*, 75:753–758, (1984).

Carpita, "Incorporation of Proline and Aromatic Amino Acids into Cell Walls of Maize Coleoptiles," *Plant Physiol.*, 80:660–666, (1986).

Nishitani and Nevins, "Dissociation of Ferulated Arabinoxylan (FAX) from Corn Cell Walls by a Novel Bacillus Subtilis Hydrolase," Abstract #639, *Plant Physiol., Supp.*, 83:106, (Apr. 1987).

Nevins, "Enzymes for Selective Dissociation of Complex Polysaccharides from Cell Walls," Abstract #25, *ACS*, (Sep. 1987).

Huber and Nevins, *Plant Physiol.*, 60:300–304, (1977).

Kato and Nevins, *Plant Physiol.*, 75:745–752, (1984).

Kato and Nevins, *Plant Physiol.*, 75:759–765, (1984).

Kato and Nevins, *Carbohydrate Research*, 137:139–150, (1985).

*Primary Examiner*—Jacqueline Stone
*Attorney, Agent, or Firm*—Townsend and Townsend

[57] ABSTRACT

This invention relates to a composition comprising a substantially pure enzyme capable of degrading arabinoxylan and having a molecular weight of about 45,000. More preferably this invention relates to such an enzyme which has a pH optimum between about 6.5 to about 7.0. The enzyme is derived from bacteria capable of hydroloyzing plant cell wall material, preferably from Bacillus most preferably from *Bacillus subtilis*. This invention further relates to such a composition which is further capable of selectively dissociating feraxan from a maize cell wall preparation. Additionally, compositions of this invention are unable to degrade Rhodymenia (1→3),(1→4)-β-D-xylan and larch arabino-(1→4)-β-D-xylan. Compositions of the present invention are capable of releasing fragments in a maize cell wall preparation at the glycosidic linkages of C1 and C5 arabinofuranosyl; C1 of terminal arabinofuranosyl; C2 and C4 of xylopyranosyl; C3 and C4 of xylopyranosyl, C1 and C3 of xylopyranosyl and C1 of terminal glucuronosyl. Compositions contemplated by the invention are also capable of releasing 2,4/3,4-linked-xylopyranosyl, terminal-arabinofuranosyl, 5-linked-arabinofuranosyl, 4-linked-xylopyranosyl, terminal-glucurono-pyranosyl and esterified ferulic acid from maize arabinoxylan. These compositions are preferably prepared from crude *Bacillus sp.* extracts by using a purification step selected from at least one of the following steps: differential precipitation using salts, ionic exchange chromatography, molecular filtration, HPLC, ultrafiltration and diafiltration.

12 Claims, 4 Drawing Sheets

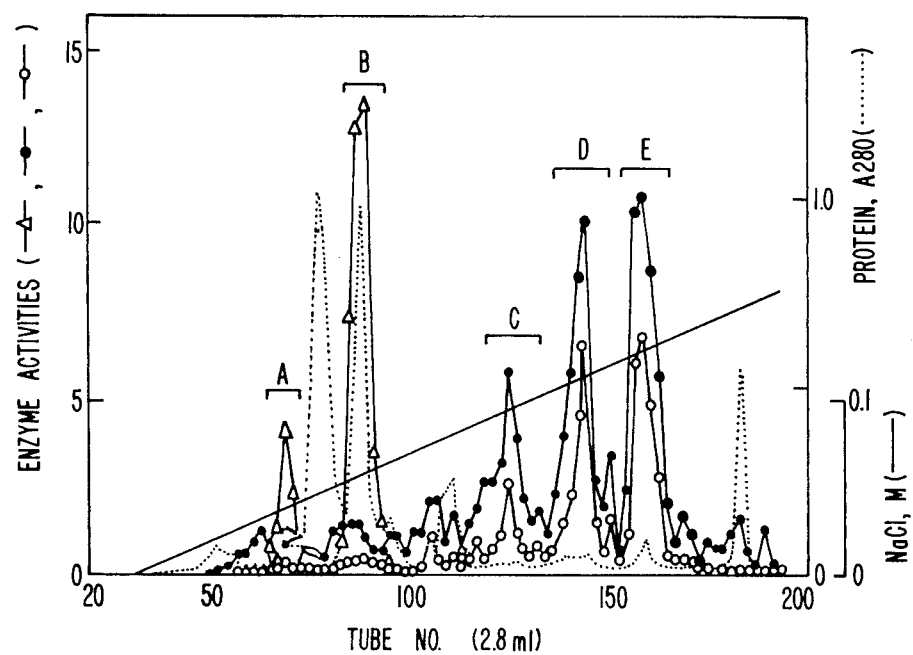
FIG._1.
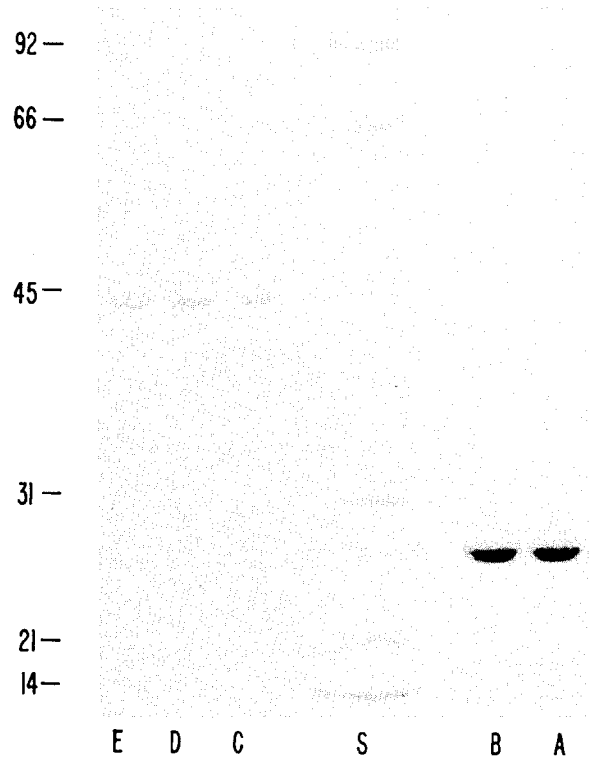
FIG._3.

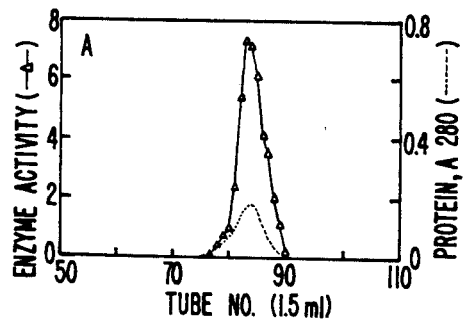
FIG._2A.
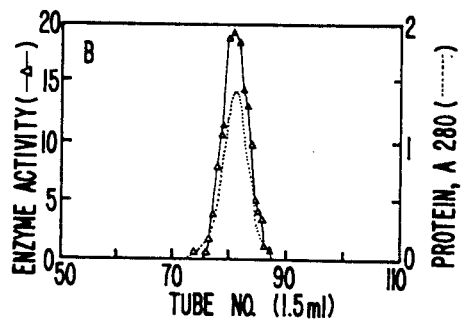
FIG._2B.
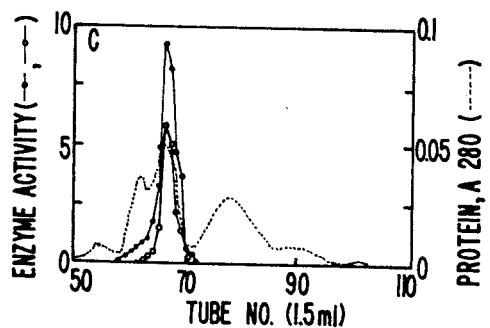
FIG._2C.
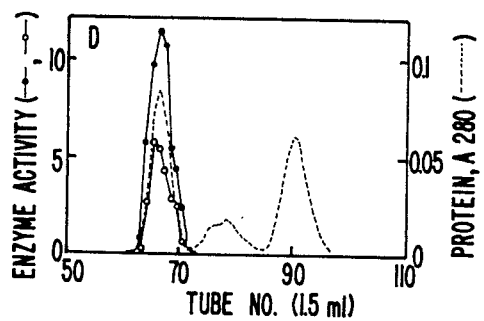
FIG._2D.
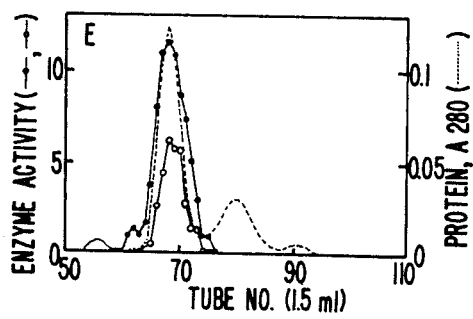
FIG._2E.

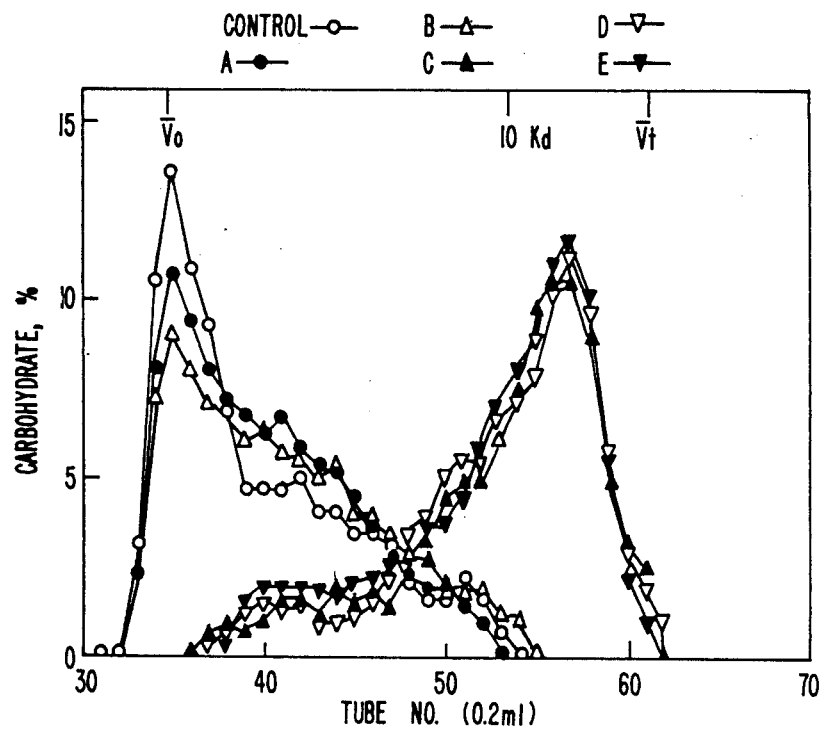
FIG._4.
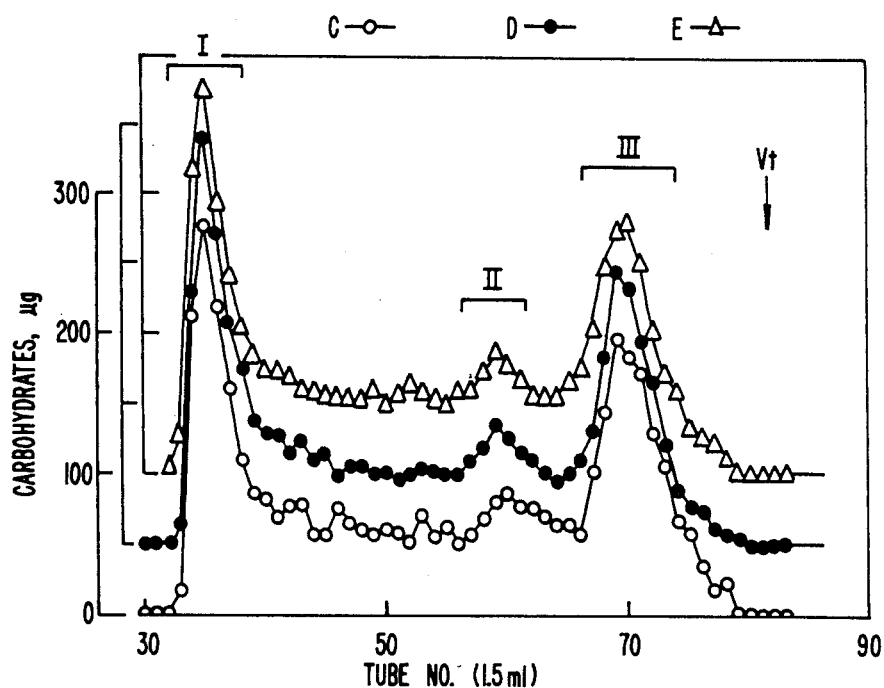
FIG._5.

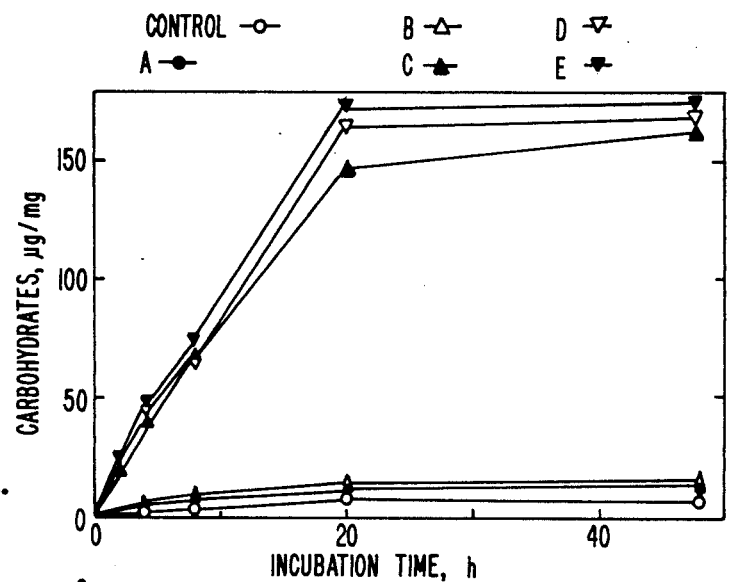
FIG._6A.
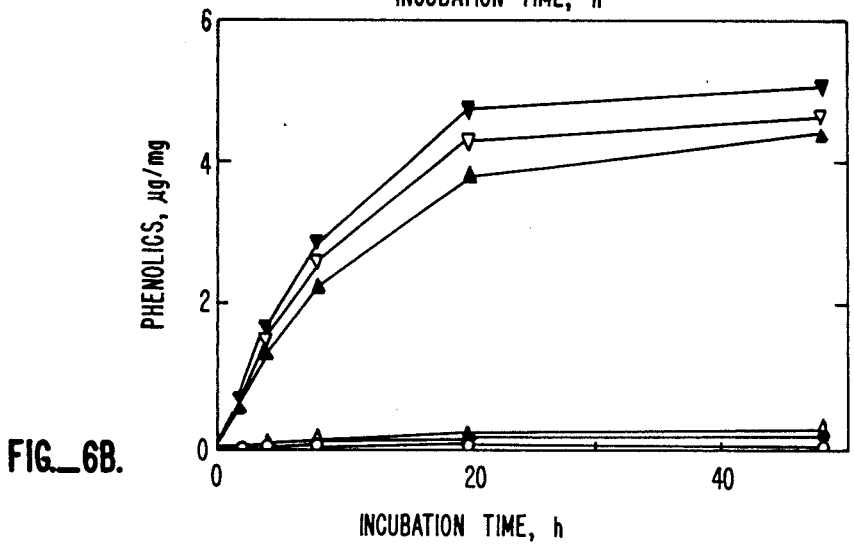
FIG._6B.

FERAXANASE, A HIGHLY SPECIFIC ENZYME FOR HYDROLYSIS OF COMPLEX POLYSACCHARIDES

BACKGROUND OF THE INVENTION

1. Field of the Invention

This invention relates to a highly specific enzyme for hydrolysis of complex polysaccharides. More specifically, there is disclosed herein novel compositions comprising, feraxanase, an enzyme capable of specifically degrading feraxan, a feruloylated arabinoxylan found in plant cell walls.

This invention was made with Government support under Grant No. DMB 85-05901 with the National Science Foundation and the University of California. The Government has certain rights in this invention.

2. Information Disclosure

The compositions of this invention selectively cleave feraxan from arabinoxylans commonly found in plant cell walls. Arabinoxylans are major components of plant cell walls, in particular cereal plant cell walls. See for example, Carpita, N.C., "Hemicellulosic Polymers of Cell Walls of Zea Coleoptiles," Plant Physiol. 72:515–521 (1983); Dubois et al., "Colorimetric Method for Determination of Sugars and Related Substances," Anal. Chem. 28:350–356 (1956); and Wilkie, "The Hemicelluloses of Grasses and Cereals," Adv. Carbohydr. Chem. Biochem. 36:215–264 (1979). Structural analyses have been conducted on arabinoxylans in an attempt to elucidate the chemical basis underlying alterations in the physical properties of the cell wall responsible for growth and development of the plant tissues. Carpita, "Cell wall Development in Maize Coleoptiles," Plant Physiol. 76:205–212 (1984); Carpita, "Incorporation of Proline and Aromatic Amino Acids into Cell Walls of Maize Coleoptiles," Plant Physiol. 80:660–666 (1986); Darvill et al., "Structure of Plant Cell Walls, XI Glucuronoarabinoxylan, a Second Hemicellulose in the Primary Cell Walls of Suspension-Cultured Sycamore Cells," Plant Physiol. 66:1135–1139 (1980); Yamamoto et al., "Effects of Auxin on the Structure of Hemicelluloses of Avena Coleoptiles," Plant Cell Physiol. 21:373–381 (1980).

Although recent studies have shown that phenolic components, particularly ferulic acid, are attached to arabinoxylans, the structure of the feruloylated-arabinoxylans (feraxan) of the cell wall has not been elucidated. In most structural studies of feraxans, alkaline solutions have been used to extract matrix polysaccharides. See, for example, Carpita, Plant Physiol. (1983); Darvill et al., Plant Physiol. (1980); Yamamoto et al.; Wilkie, all supra. Alkaline extraction, however, results in not only nonselective liberation of matrix polysaccharides but in undersirable cleavage of certain covalent bonds, particularly ester linkages through which phenolic acids are attached to arabinoxylans.

To avoid the problems encountered in the alkaline extraction procedures, selective dissociations of cell wall fragments by purified enzymes with known specificities have been used. Most success thus far has been reported for the pectic polysaccharides. See, Talmadge et al., "The Structure of Plant Cell Walls I.," Plant Physiol. 51:158–173 (1973). Success has also been reported with (1→3), (1→4)-β-D-glucans. Huber and Nevins, "Preparation and Properties of a β-D-glucanase for the Specific Hydrolysis of β-D-glucans." Plant Physiol. 601:300–304 (1977).

In order to better understand the role of arabinoxylans in the overall scheme of plant cell wall structure, enzymes having selective sites of polymer cleavage are needed. At present, Kato and Nevins have purified a (1→4)-β-D-xylanase capable of degrading feraxan of maize cell wall from a B. subtilis enzyme preparation. This enzyme, however, had limited action in dissociating feraxan from the maize cell wall. Only about 10% of feraxan present in the wall was released. Kato and Nevins, "Enzymic Dissociation of Zea Shoot Cell Wall Polysaccharides, III," Plant Physiol. 75:753–758 (1984). Thus, there is a need for additional enzymes for use in cell wall structural analysis. In addition there is a need for selective enzymes for use in biomass conversion of plant material from waste into animal feed as undigestible carbohydrates are enzymatically converted to digestible sugars. Novel enzyme systems are also needed for production of specific sugars from polymers. Finally, there is a growing need for selective enzymes able to partially digest cell walls of plants to facilitate genetic transformations using recombinant genetics.

SUMMARY OF THE INVENTION

This invention relates to a composition comprising a substantially pure enzyme capable of degrading arabinoxylan and having a molecular weight of about 45,000. More preferably this invention relates to such an enzyme which has a pH optimum between about 6.5 to about 7.0. The enzyme is derived from bacteria capable of hydrolyzing plant cell wall material, preferably from Bacillus sp. most preferably from Bacillus subtilis. This invention further relates to such a composition which is further capable of selectively dissociating feraxan from a maize cell wall preparation. Additionally, compositions of this invention are unable to degrade Rhodymenia (1→3), (1→4)-β-D-xylan and larch arabino-(1→4)-β-D-xylan. Compositions of the present invention are capable of releasing fragments in a maize cell wall preparation which comprise the glycosidic linkages of C1 and C5 arabinofuranosyl; C1 of terminal arabinofuranosyl; C2 and C4 of xylopyranosyl; C3 and C4 of xylopyranosyl, C1 and C3 of xylopyranosyl and C1 of terminal glucuronosyl. Compositions contemplated by the invention are also capable of releasing 2,4/3,4-linked-xylopyranosyl, terminal-arabinofuranosyl, 5-linked-arabinofuranosyl, 4-linked-xylopyranosyl, terminal-glucurono-pyranosyl and esterified ferulic acid from maize arabinoxylan. These compositions are preferably prepared from crude Bacillus sp. extracts by using a purification step selected from at least one of the following steps: differential precipitation using salts, ionic exchange chromatography, molecular filtration, HPLC, ultrafiltration and diafiltration.

DESCRIPTION OF THE FIGURES

FIG. 1: CM-Sepharose CL-6B chromatography of enzyme preparation 4 (Table 1). Enzyme preparation 4 (17.2 mg protein) was separated on a CM-Sepharose CL-6B column. Fractions were assayed for β-xylanase activity (open triangles), feraxan dissociating activity (solid circles for total carbohydrates, open circles for total phenolics) as well as protein content (dotted line). Enzyme preparation-5A (tube Nos. 65–72), -5B (84–92), -5C (119–136), -5D (137–153) and -5E (154–167) were collected and concentrated.

FIG. 2: Gel filtration chromatography of enzyme preparations-5A, -5B, -5C, -5D and -5E. Individual enzyme preparations were chromatographed on a Bio Gel P-10 column. For enzyme preparations-5A and -5B $\beta$-xylanase activity (open triangles) as well as protein content (dotted line) were assayed. For enzyme preparations-5C -5D and -5E, feraxan-dissociating activity (solid circles for total carbohydrates, open circles for total phenolics) as well as protein content (dotted line) were assayed.

FIG. 3: SDS-PAGE of enzyme preparations-A, -B, -C, -D and -E. Individual enzyme preparations (A, B, C, D, and E) (5 $\mu$g each) and a mixture of standard proteins (S) (2 $\mu$g each) were separated on a 10% SDS-PAGE. After electrophoresis the gels were stained by Coomassie Brilliant Blue 25R.

FIG. 4: Resolution by gel filtration on a TSK Gel G 4000PW column of enzyme hydrolyzates derived from maize arabinoxylan (MAX). MAX (3 mg each) was dissolved in 1 ml of 20 mM Na-phosphate buffer solution (pH 6.8) containing 0.05% sodium azide and incubated with 1 $\mu$g of enzyme preparation-A or -B, or with 0.2 $\mu$g of preparation-C, -D or -E. For controls, a mixture of the five enzyme fractions were boiled and used. After three hours of incubation at 37° C., individual reaction mixtures were boiled for 5 min. and separated by HPLC on a TSK Gel G 4000 PW column. After chromatography, each tube was assayed for total carbohydrate content and expressed as percentages of the total carbohydrate applied.

FIG. 5: Bio Gel P-10 chromatograms of enzyme hydrolyzates of MAX. MAX (4 mg each) dissolved in 1 ml of 20 mM Na-phosphate buffer solution (pH 6.8) containing 0.05% sodium azide was incubated with 0.2 $\mu$g of enzyme preparation-C, D, and E at 37° C. for 24 h. Individual reaction mixtures were boiled for 5 min and separated on a Bio Gel P-10 column. Each tube was assayed for total carbohydrate content. For the control, a mixture of five enzyme preparations was boiled and used.

FIG. 6: Time course for dissociation of feraxan from maize coleoptile sections by purified enzyme preparations. Maize coleoptile sections (10 mg each) were rehydrated in 2 ml of 20 mM Na-phosphate buffer solution (pH 6.8) containing 0.05% sodium azide and incubated with 1 $\mu$g of enzyme fraction-A or -B, or with 0.2 $\mu$g of enzyme preparation-C, -D or -E, at 37° C. At intervals, a portion of the incubation mixture was assayed for total carbohydrate content and total phenolic content.

DETAILED DESCRIPTION OF THE PREFERRED EMBODIMENTS

Enzymes designated feraxanases, exclusively remove one major xylan component of native plant cell walls—feraxan. Feraxanases will be useful in contributing to effective biomass conversion and may facilitate gene transfer by reducing resistance caused by the cell wall structure as the enzymes are capable of producing "pores" in the wall without other apparent injury. Feraxanases will also have applicability in protoplast preparation of cereal plants.

A. Source of Feraxanase

Feraxanase is purified from a Bacillus sp. enzyme preparation. Commercially available crude preparations of Bacillus enzymes produced by submerged fermentation of selected strains of *B. subtilis* such as that produced by Novo Industri (Copenhagen, Denmark) and sold under the trade name of Novo Ban L-120 are the most convenient and most preferred enzyme preparations. Alternatively Bacillus may be cultured under well known conditions and the nutrient media supporting the growth of the bacteria may be collected and used as a source of the enzyme or whole bacterial cells may be lysed and used. The extract can then be used directly in the purification procedures described below or concentrated first by standard techniques (e.g., ultrafiltration, evaporation).

B. Purification of Feraxanase

1. Insoluble material is first removed from the crude enzyme preparation described above by dialyzing the preparation against a buffer solution and then utilizing other methods well known in the art such as ultrafiltration, column chromatography and centrifugation. The choice of buffer is not critical. Typically, the buffer is a low molarity buffer having a buffering capacity at a physiological pH range of from about 6.0 to about 8.0, most preferably from about 6.0 to about 7.0. The preferred buffer is a sodium phosphate buffer, though other buffers well known in the art may be used including Tris-hydrochloride or sodium citrate.

2. The preparation is next precipitated by using standard techniques known in the field, such as the use of cold acetone or salts. Concentrations and other conditions vary in accordance with the salt chosen. Standard experimental strategies can be used to optimize selective precipitation for each salt. Selective precipitation using solutes is preferred. Such solutes include Guanidine-HCl and urea. Most preferred is the use of ammonium sulfate. The precipitate is then collected and redissolved in a suitable buffer of low molarity and neutral pH such as previously described. Remaining salts are removed by exchange of buffer using standard techniques; for example, ultrafiltration, column chromatography or dialysis.

3. The preparation is then further purified using standard column chromatographic techniques which may include, for example, ion exchange chromatography, molecular filtration, electrophoresis, isoelectricfocusing or high performance liquid chromatography (HPLC). Standard columns generally recognized for use in purifying proteins are contemplated in purifying the enzyme of the present invention and many alternative columns are commercially available and known to those skilled in the art. Preferred examples include DEAE-Sephacel and CM-Sepharose, DEAE cellulose, CM cellulose, CM cellulose or other anionic and cationic media (Sigma Chemical Co., St. Louis, Mo.).

Typically the preparation is passed through at least one ion exchange filter preequilibrated with one of the buffers described above and eluted using the same buffer. The enzyme can be concentrated and applied to a second ion exchange filter for further purification. Buffers as previously described may be used for preequilibration and elution.

4. For additional purification, the preparation may be concentrated by methods well known in the art such as dialysis or ultrafiltration and placed directly on an ion exchange column such as those described above. Typically the column is washed with a buffer solution as described above, followed by elution with a salt solution such as sodium chloride. Elution with the salt solution is preferably done at varying concentrations through the course of elution. For example, salt solutions of different concentrations can be passed through the column at different times or elution could be accomplished by using a linear gradient of a salt solution. More specifically using a DEAE Sephacel column, the enzyme can be eluted from the column using a low molarity buffer of about .01 to 0.05M. The feraxanase component may be added to a CM Sephadex column and recovered by increasing the ionic strength of the eluting buffer to a range of about 0.3M to 1M NaCl. The specific concentrations for particular buffer systems and gels are readily obtained using standard experimental strategies.

The order of steps 3 and 4 are not critical. Preferably an anion exchange column such as DEAE-Sephacel is used in one step and a cation exchange column such as CM-Sepharose is used in the other step.

5. Optionally the enzyme preparation may be further purified by passing the preparation through a molecular filtration-type column using a buffer as described above which contains a low molar salt solution. Examples of molecular filtration devices include Bio Gel P-10 (Bio-Rad Laboratories, Richmond, CA) and Sephadex G-50 (Pharmacia, Piscataway, NJ). Preferably a second such rechromatographing is performed. This step enables one to determine the purity and molecular size of the enzyme preparation.

6. Purified feraxanase preparations may be stored in a buffered solution, preferably containing a low molar salt solution such as sodium chloride and a preservative such as sodium azide.

C. Monitoring of the Enzyme Preparation

Throughout the purification of the enzyme, the preparation samples may be monitored to determine the location of the enzyme in the samples collected. The samples may be monitored using optical density (280 nm), immunoassay techniques, absorbance ratios or by standard protein assays such as Lowry tests or other commercially available assay tests for protein. These methods are all readily known in the art. Preferably, the assays will involve the monitoring of enzymatic activity on specific substrates as described below.

D. Feraxanase Activity

The feraxanase of this invention, is a homogeneous, endo-type hydrolase which has a molecular weight of about 45000. It has a pH optimum range between about 6.0 to about 8.0, preferably from about 6.0 to about 7.0 as determined by using McIlvaine buffers (pH 2.5 to 8.0) at 37° C. See, McIlvaine, T. C., "A Buffer Solution for Colorimetric Comparison," J. Biol. Chem. 49:183–186 (1921). The enzyme, as an endo-type hydrolase, is able to degrade native substrate into relatively large fragments. Feraxanase results in nearly complete recovery of feraxan in a short time and it exhibits high specificity.

Feraxanase is capable of degrading maize arabinoxylan (MAX). MAX is a standard complex of carbohydrates useful for comparison purposes. MAX is prepared from maize plant material, preferably coleoptile sections from which pectin is generally removed. The pectin may be removed by extraction with an ammonium oxalate-oxalic acid buffer and heat. The MAX preparation may also be further treated with a glucanase digestion to remove $\beta(1\rightarrow3)$, $(1\rightarrow4)$ mixed linked glucans. MAX is then precipitated by the addition of ethanol to acidified MAX. Based on linkage analyses generated by the action of feraxanase, the resulting standard, MAX, likely has a repeating unit with a degree of polymerization of about 10 which contains glucuronosyl, arabinosyl and arabinosyl-$(1\rightarrow5)$-arabinosyl residues.

Feraxanase is a glucuronoarabino-$\beta$-$(1\rightarrow4)$-xylan xylanohydrolase. It is highly specific for MAX and is unable to degrade Rhodymenia $(1\rightarrow3)$, $(1\rightarrow4)$-$\beta$-D-xylan or larch arabino-$(1\rightarrow4)$-$\beta$-D-xylan. Feraxanase is also unable to degrade cellulose, carboxymethycellulose, lichenan, oat $\beta$-glucan, barley $\beta$-glucan, laminarin, dextran, starch, citrus pectin, maize pectin, polyuronides, arabinan, galactan, arabinogalactan, yeast mannan, and galactomannan under the conditions set forth in the example below.

The major sugar fragments released from MAX after treatment with feraxanase have one or more of the following linkages: terminal arabinofuranosyl, 5-linked-arabinofuranosyl, 4-linked-xylopyranosyl, 3,4 and/or 2,4-linked xylopyranosyl and terminal glucuronosyl residues. Feraxanase does not release detectable levels of monomers, dimers, trimers, or tetramers of xylose and/or arabinose in MAX as analyzed by HPLC.

The compositions of feraxanase described herein are substantially pure. A substantially pure enzyme is defined herein as an enzyme which migrates largely as a single band in standard electrophoresis gels or largely as a single peak when monitored on a chromatographic column. More specifically, compositions of substantially pure enzymes have less than ten percent miscellaneous proteins. Miscellaneous proteins include degraded proteins from intact feraxan or arabinoxylan and proteins or peptides unrelated to feraxan or arabinoxylan. Typically by using the procedures described above or by following the examples below, preparations of feraxanase are achieved that are greater than 95% pure as assayed by standard techniques. However, by repeating the above purification steps even greater levels of purity can be achieved such that the percent purity approaches the theoretical limit of 100%.

The compositions described herein comprise a selective enzyme. A selective enzyme is capable of "selectively dissociating" components by virtue of its ability to recognize specific glycosidic linkages. Feraxanase is an enzyme capable of selectively dissociating more than 50% of the feraxan from a maize cell wall preparation.

The specific activity of a substantially pure feraxanase composition is defined as a composition capable of degrading alkaline-extracted MAX at greater than about 0.009 units/mg, preferably at greater than 0.100 units/mg, and most preferably at greater than 0.700 units/mg. Units/mg refers to enzyme activity units per milligrams of protein. Enzyme activity units are determined by the number of reducing groups which are detected as a result of the cleavage of the carbohydrate bonds. Alternatively, the substantially pure feraxanase composition can be characterized as one which demonstrates a greater than 2-fold, preferably a greater than 25-fold, and most preferably a greater than 100-fold activity over the crude extract described in step one when applied to alkaline-extracted MAX. It is noted that the specific activity of the Novo Ban L-120 product is considered as a standard starting material against which other materials are measured.

Feraxanase is further capable of liberating most of the arabinose, xylose and ferulic acid in maize coleoptile sections pretreated by boiling in 80% ethanol with lesser amounts of uronic acid, galactose and glucose being released. Feraxanase is not capable of releasing fucose or mannose from such tissue.

Other plant material with a similar carbohydrate structure to MAX or to maize coleoptile sections can be suitable substrate material for assaying or detecting feraxanase, particularly other monocotyledonous plant material.

It is contemplated that the novel compositions of this invention specifically include both natural forms of feraxanase as well as variants created by modern genetic technology such as recombinant genetics. It is likely that naturally occurring variants of feraxanase exist. Such variants could arise from spontaneous mutations from a theoretical seminal enzyme form. These heteroallelic forms have minor amino acid residue differences from the seminal enzyme and these forms have similar, if not identical, biological properties to each other. Further, using recombinant genetics it would be routine to create derivatives of the feraxanase disclosed herein which would have similar biological properties. Such derivatives may include peptide fragments and amino acid deletions or additions within the natural amino acid sequence for feraxanase. For example, it is known in the protein art that certain amino acid residues can be substituted with amino acids or similar size and polarity without an undue effect upon the biological activity of the protein.

EXPERIMENTAL

I. Purification of Feraxanase

The *Bacillus subtilis* enzyme preparation Novo Ban L-120 industrial amylase preparation was obtained from Novo Industri A/S (Copenhagen, Denmark). Novo Ban L-120 (400 ml) was dialyzed against 10 mM Na-phosphate buffer (pH 6.3) followed by centrifugation for 30 min at 10,000×g to remove insoluble material. The supernatant (1.5L) was reduced to 200 ml by ultrafiltration (Enzyme preparation 1; 2.28 g protein).

Enzyme preparation 1 was fractionated by ammonium sulfate precipitation. The precipitate between 40 to 60% saturation was collected, dissolved in the Na-phosphate buffer solution, and then dialyzed against the same buffer solution (Enzyme preparation 2; 713 mg protein).

Enzyme preparation 2, in 100 ml of the Na-Phosphate buffer, was applied to a column of DEAE-Sephacel (65 mm×80 mm) (Sigma Chemical Co.) which had been preequilibrated with the 10 mM Na-phosphate buffer solution. Elution was accomplished with the same buffer solution. Most of the MAX-degrading activity and feraxan-dissociating activity (feraxanase activity) as well as β-xylanase activity was recovered in the first 200 ml of the elute (Enzyme preparation 3; 261 mg protein). This fraction was reduced to 10 ml and applied to a longer DEAE-Sephacel column (25 mm×900 mm) (Sigma) preequilibrated and eluted with the same buffer solution. Nine ml fractions were collected and assayed for MAX-degrading activity, feraxanase activity and β-xylanase activity. The active fractions (tube Nos. 27 and 28) were collected and concentrated to 3 ml (Enzyme preparation 4; 171 mg).

Enzyme preparation 4 was applied to a column of CM-Sepharose CL-6B (18×450 mm) (Sigma) preequilibrated with 10 mM Na-phosphate buffer solution (pH 6.3). The column was washed with 200 ml of the same buffer solution followed by elution with a linear gradient of NaCl (0 to 0.2M) in the Na-phosphate buffer. No β-xylanase or feraxanase activity was detected in the first 200 ml of the eluate. Subsequently, fractions of 2.8 ml were collected and assayed for β-xylanase activity and feraxanase activity. Two distinct β-xylanase fractions (Enzyme preparations 5-A, 5-B) and three feraxanase fractions (Enzyme preparations 5-C, 5-D, 5-E) were separately collected and concentrated (FIG. 1).

The five fractions were separately chromatographed on a Bio Gel P-10 column (Bio-Rad Laboratories) using the 10 mM Na-phosphate buffer containing 0.2M NaCl as the eluent. The protein peaks which coincided with the individual enzyme activities were rechromatographed under the same conditions (FIG. 2) and stored in a 10 mM Na-phosphate buffer solution containing 0.2M NaCl and 0.05% sodium azide at 4C (Enzyme preparations A, B, C, D and E). The data summarizing the purification of these enzyme preparations are shown in Table 1.

TABLE 1

Summary of Purification of B. Subtilis Hydrolases

| Purification steps | Enzyme preparation | Protein | Total activity | Specific activity | Recovery of activity | Purification |
|---|---|---|---|---|---|---|
| | | | β-xylanase activities [a] | | | |
| | | mg | K units | K units/mg | % | fold |
| Dialysis | 1 | 2278 | 286 | 0.126 | 100 | 1 |
| Amm. sulfate | 2 | 713 | 128 | 0.180 | 44.8 | 1.43 |
| DEAE-Sephacel, 1st | 3 | 261 | 74.7 | 0.286 | 26.1 | 2.28 |
| DEAE-Sephacel, 2nd | 4 | 17.2 | 69.0 | 4.01 | 24.1 | 31.9 |
| CM-Sepharose | 5-A | 0.27 | 7.3 | 27.0 | 2.5 | 214 |
| | 5-B | 3.96 | 42.0 | 10.6 | 14.7 | 84.1 |
| Bio Gel P-10 | A | 0.19 | 5.25 | 27.6 | 1.8 | 220 |
| | B | 2.4 | 36.4 | 15.2 | 12.7 | 121 |
| | | | MAX-degrading activities [b] | | | |
| | | mg | K units | K units/mg × $10^{-3}$ | % | fold |
| Dialysis | 1 | 2278 | 11.5 | 5.04 | 100 | 1 |
| Amm. sulfate | 2 | 713 | 3.97 | 5.57 | 34.6 | 1.11 |
| DEAE-Sephacel, 1st | 3 | 261 | 2.40 | 9.18 | 20.9 | 1.82 |
| DEAE-Sephacel, 2nd | 4 | 17.2 | 2.17 | 126 | 19.0 | 25.1 |
| CM-Sepharose | 5-C | 0.46 | 0.32 | 700 | 2.88 | 139 |
| | 5-D | 0.69 | 0.74 | 1076 | 5.40 | 213 |
| | 5-E | 0.50 | 1.02 | 2030 | 8.28 | 403 |
| Bio Gel P-10 | C | 0.13 | 0.26 | 2015 | 2.35 | 400 |
| | D | 0.27 | 0.59 | 2200 | 4.32 | 436 |

TABLE 1-continued
Summary of Purification of *B. Subtilis* Hydrolases

| Purification steps | Enzyme preparation | Protein | Total activity | Specific activity | Recovery of activity | Purification |
|---|---|---|---|---|---|---|
| | E | 0.39 | 0.87 | 2238 | 7.12 | 444 |

[a] β-xylanase activity was determined using Rhodymenia xylan as the substrate.
[b] MAX-degrading activity was determined using alkaline-extracted maize arabinoxylan (MAX) as the substrate.

Concentration of enzyme preparations was carried out by ultrafiltration using a YM-5 membrane (Amicon, Danvers, MA). Dialysis of enzyme preparations was performed using Spectra/por 3 (Spectrapor, Los Angeles, CA) (MW cut off 3500). Protein content was estimated using the Bradford Protein Assay (Bio-Rad Laboratories) with bovine serum albumin (BSA) as a standard or by UV absorption at 280 nm.

II. Enzyme Activity

A. Preparation of enzyme substrates

1. Preparation of dry coleoptile sections

Fresh coleoptile sections (1 cm long) excised from maize (*Zea mays* L. hybrid B73×Mo17, seed from Braton Seed Co. Ames, IA) seedlings which had been grown in darkness at 25° C. for 5 days were boiled in 80% aqueous ethanol for 10 min. Boiled coleoptile sections were washed sequentially with ethanol, acetone, a methanol-chloroform mixture (1/1,v/v) and ethanol. The sections were rehydrated and soaked in 3M LiCl solution at 10° C. for 2 days followed by extensive washing with water. They were then incubated in a porcine pancreatic α-amylase (Sigma Type 1-A) solution (100 μg in 100 ml or 10 mM Na-phosphate buffer solution, pH 7.0) in the presence of 0.05% sodium azide at 35° C. for 24 h followed by extensive washing with water to remove starch. The sections were dehydrated with ethanol and acetone, dried in vaccuo and weights of dry coleoptile sections were recorded.

2. Maize pectin and arabinoxylan

Maize pectin and arabinoxylan were prepared from the dry coleoptile sections: The dry coleoptile sections were rehydrated and homogenized in 20 mM ammonium oxalate-oxalic acid buffer (pH 4.0), then heated at 70° C. for 30 min to extract the pectin fraction. The extraction was repeated four times and extracts combined, mixed with 2 volumes of ethanol and maintained overnight at −20° C. The precipitate was centrifuged, dissolved in water, dialyzed against water and lyophilized to obtain maize pectin.

After the pectin extraction, the cell wall residue as suspended in the purified (1→3), (1→4)-β-D-glucan-4-glucanohydrolase (β-glucanase) solution (10 μg glucanase in 100 ml of 10 mM Na-phosphate buffer solution, pH 6.8 with 0.05% sodium azide) then incubated at 35° C. for 24 h to remove β(1→3), (1→4) mixed linked glucans followed by extensive washing with water. After the glucanase digestion, the residue was extracted three times with 4% KOH aqueous solution at 25° C. for 8 h. The extract was combined and acidified with 0.06 volumes of glacial acetic acid. Four volumes of ethanol were added to the acidified solution to precipitate maize arabinoxylan (MAX). The precipitate was dissolved in water, dialyzed against water and lyophilized to obtain MAX.

β-glucanase was purified from a *Bacillus subtilis* α-amylase preparation (Novo Ban L-120) by a procedure similar to that described by Kato and Nevins in "Enzymic Dissociation of Zea Shoot Cell Wall Polysaccharides II". Dissociation of (1→3), (1→4)-β-D-glucan-4-glucanohydrolase from *Bacillus subtilis*, Plant Physiol. 75:745–752 (1984) using Cellex-D (DEAE-cellulose, Bio-Rad Laboratories) and Bio Gel P-10 (Bio-Rad) chromatography.

3. Xylan

A (1→3), (1→4)-β-D-xylan was purified from *Rhodymenia palmata* fronds by the method of Kato and Nevins described in "Enzymic Dissociation of Zea Shoot Cell Wall Polysaccharides III". Purification and partial characterization of an endo-(1→4)-β-D-xylanase from a *Bacillus subtilis* enzyme preparation Plant Physiol. 75:753–758 (1984) with one modification: Rhodymenia fronds (10 g) were extracted twice with 200 ml of boiling water. The extract was mixed with 2 volumes of methanol and centrifuged to obtain 2.7 g of precipitate. The precipitate (2.5 g) was dissolved in 250 ml of 20 mM Na-acetate buffer solution pH 5.3 and applied to a DEAE-cellulose (17 g dry weight) column (Bio-Rad Laboratories) which had been equilibrated with the same buffer solution. The column was eluted with the same solution. The first 800 ml of the eluate was collected and mixed with 2 volumes of ethanol. The precipitate thus obtained was washed with ethanol and acetone and dried in vaccuo to obtain 1.5 g of pure xylan.

4. Larch Arabinoxylan

Larch arabinoxylan (Sigma Chemical Co.) was purified by the method described by Taiz and Honigman in "Production of Cell Wall Hydrolyzing Enzymes by Barley Aleurone Layers in Response to Gibberellic Acid," Plant Physiol. 58:380–386 (1976).

5. Glucan

A (1→3), (1→4), -β-D-Glucan was extracted from oat bran (The Quaker Oat Company, Barrington, IL). Oat bran was boiled in 80% aqueous ethanol solution, washed with acetone and then dried. The dried bran was extracted three times for 30 min each with water at 45° C. After the extract was digested with a pancreatic α-amylase solution, β-glucans were precipitated by ammonium sulfate (between 20–40% saturation) followed by dialysis against water and lyophilization.

B. Enzyme assays

β-xylanase activity and MAX-degrading activity were assayed using Rhodymenia xylan and MAX respectively: 0.4 ml of 20 mM Na-phosphate buffer solution (pH 5.4) containing 0.2% Rhodymenia xylan or MAX was incubated with 5 μl of enzyme preparation at 37° C. and the reaction was terminated by the addition of the Somogyi reagent. Reducing sugars liberated during the reaction were determined by the methods of Somogyi and Nelson. (See Somogyi, M. "Notes on Sugar Determination", J. Biol. Chem. 95:19–23 (1952) and Nelson, N. J., "A Photometric Adaptation of the Somogyi Method for the Determination of Glucose", J. Biol. Chem. 153:375–380 (1944), both of which are incorporated by reference herein). One unit of the enzyme activity was defined as equivalent to the liberation of 100 μg of xylose equivalents in the first 10 min under the conditions described above.

Feraxanase activity was assayed using the dry coleoptile sections of maize as the substrate: Two sections of maize coleoptile cell wall (ca. 1.2 mg) were rehydrated in 1 ml or 20 mM Na-phosphate buffer solution (pH 6.8) and incubated with 5 μl of the enzyme preparation in the presence of 0.05% sodium azide at 37° C. for 12 h. After the reaction, a portion of the solution was assayed for total carbohydrate by the phenolsulfuric acid method described below and for the total phenolic compounds by UV absorption at 324 nm. The enzyme activity was expressed as total carbohydrate (xylose equivalents) liberated under the conditions described above.

The phenol-sulfuric acid method comprised saponifying the enzyme hydrolyzates or dry coleoptile sections in 0.5M NaOH solution under nitrogen at 60° C. for 90 min. After the saponification the alkaline solution was acidified by addition of 1.1 volumes of 0.05M HCl solution then applied to a Sep Pak C18 cartridge (Waters Associates, Milford, MA), which had been swollen by 10 ml of ethanol and equilibrated with 10 ml of water containing 0.05% acetic acid. The cartridge was washed successively with 10 ml of water containing 0.05 acetic acid and 5 ml of 10% ethanol solution containing 0.05% acetic acid. The phenolic acids were then eluted by 5 ml of 90% ethanol solution. The amount of total phenolic compounds was estimated by the measurement of UV absorption of the eluate at 324 nm and converted to ferulic acid equivalents.

To analyze neutral sugar compositions oligo-or polysaccharides (ca. 50 μg) were hydrolyzed with 2M trifluoroacetic acid (TFA) at 120° C. for 1 h. After the acid was removed with a stream of air, the sugars were converted into their corresponding alditol acetates as described in Albersheim et al., "A Method for the Analysis of Sugars in Plant Cell Wall Polysaccharides by Gas-Liquid Chromatography," Carbohydr. Res. 5:340–345 (1976) which is incorporated by reference herein, followed by analysis using gas liquid chromatography equipped with an SP 2330 glass WCOT capillary column. The column temperature was increased from 150° to 225° by 4° C. per min.

Uronic acid (UA) compositions of the enzyme hydrolyzates were determined by reducing the carboxyl groups in the polysaccharides as described in Anderson et al., "A Radiochemical Approach to the Determination of Carboxylic Acid Groups in Polysaccharides," Carbohydr. Polymers 5:115–129 (1985), which is incorporated by reference herein, before TFA hydrolysis. Analysis was by the same procedure as for neutral sugars.

Total uronide content of the enzyme hydrolyzates was determined by the procedure of Blumenkrantz and Asboe-Hansen, "New Method for Quantitative Determination of Uronic Acids," Anal. Biochem. 54:484–489 (1973), incorporated by reference herein.

A portion of the eluate was evaporated under a stream of nitrogen and dissolved in 20% acetonitrile solution with 0.05% acetic acid. Phenolic acids were separated by HPLC on a biosil ODS-5S column (4×250 mm, Bio-Rad Laboratories). The phenolic compounds were eluted at a rate of 1 ml/min with 20% acetonitrile and 80% water with 0.05% acetic acid for 10 min, followed by an increase to 40% acetonitril during the next 10 min. Then, the eluate was held at 40% acetonitrile during the next 20 min. Phenolic acids were monitored by a UV detector at 310 nm and identified by retention time: 9.37 min for p-coumaric acid, 9.65 min for ferulic acid and 22.53 min for diferulic acid. The eluate containing ferulic acid was collected, evaporated under a stream of nitrogen and identified by solid probe mass spectrometry at 70 eV.

Methylation analysis.

Lyophilized oligo- or polysaccharide (ca. 200 μg) was methylated with K-dimethylsulfinyl anion and was methyl iodide as described in Hakomori, S. "A Rapid Permethylation of Glycolipid and Polysaccharide Catalyzed by Methylsulfinyl Carbanion in Dimethyl Sulfoxide", J. Biochem. 55:205–208 (1964) which is incorporated by reference herein. The permethylated oligo- or polysaccharide was purified using a Sep Pak C18 as described in Carpita, NC "Cell Wall Development in Maize Coleoptiles." Plant Physiol 76:205–212 (1984), incorporated by reference herein, hydrolyzed in 2M TFA, reduced with NaBD4, then acetylated as described in Albersheim et al., supra. Partially methylated alditol acetates were analyzed on a 30 m DB 225 fused silica capillary column (J & W Scientific, Rancho Cordova, California) maintained isothermally at 220° C. with a split ratio of about 40:1 using helium as a carrier gas (1 ml/min). Injector and FID temperatures were set at 180° C. and 230° C. respectively. Gas Chromatography-Mass Spectrometry was also performed with a mass-spectrometer equipped with the same DB 225 column by electron impact at 70 eV (election volts).

Gel filtration of enzyme digestion products

Enzyme digestion products were analyzed by three different chromatographic systems: (1) Neutral oligosaccharides in enzyme digests of Avena β-glucan, Rhodymenia xylan and MAX were analyzed by HPLC (Bio-Rad Model 1330) on an Aminex carbohydrate HPX 42A column (7.8×300 mm) (Bio-Rad Laboratories). Carbohydrates were eluted with water at 0.6 ml/min at 50° C. and monitored by a differential refractometer (Bio-Rad Model 1770). (2) Enzyme hydrolyzates of MAX were separated by HPLC on a TSK Gel G 4000 PW column (7.5×300 mm+7.5×75 mm) Bio Rad Laboratories. The hydrolyzate was eluted with 0.1M Na-acetate buffer solution (pH 5.4) at 1 ml/min. Fractions (0.2 ml) were collected and assayed for the total carbohydrate by the phenol-sulfuric acid method; (3) Enzyme hydrolyzate of MAX was also separated by a Bio Gel P-10 (200–400 mesh) column (15×900 mm) (Bio-Rad Laboratories). The hydrolyzate was eluted with 50 mM Na-acetate buffer solution (pH 5.4) at 7 ml/h. Fractions (1.5 ml) were collected and assayed for the total carbohydrate by the phenol-sulfuric acid method.

The concentration of carbohydrate in solution was performed by rotary evaporation under reduced pressure at 35° C. or by a stream of filtered air at 40° C. Carbohydrate solutions were desalted either by dialysis against water using Spectra/por 6 (MW cut off 2000) or by a Bio Gel P-2 gel chromatography (20×400 mm) (Bio-Rad Laboratories) using water as an eluent. Drying of desalted carbohydrate solutions was performed by lyophilization.

Electrophoresis

SDS-PAGE was performed using 0.75×140×140 mm discontinuous polyacrylamide gels by the procedure of Laemmli, UK "Cleavage of Structural Proteins During the Assembly of Head of Bacteriophage T4," Nature 227:680–685 (1970) which is incorporated by reference herein. Five μg each of purified enzymes in a sample buffer (0.125M Tris-HCl, pH 6.8; 4% SDS; 10%

2-mercaptoethanol) was subjected to SDS-PAGE. After the electrophoresis, the gel was stained by Coomassie Brilliant Blue 25 R.

C. Characterization of purified enzymes

SDS-PAGE of individual enzyme preparations indicated that the three feraxanase preparations (Enzyme preparations C, D and E) are homogeneous and have a common MW of 45,000. The two β-xylanases (Enzyme preparation A and B) have a common MW of 27000 and are mostly associated with a single band (FIG. 3). Protein standards for SDS-PAGE MW estimation were obtained from Bio-Rad Laboratories.

None of these enzyme preparations showed activity on polysaccharides including cellulose (Nutritional Biochem. Corp., Cleveland, Ohio), carboxymethyl-cellulose Type 7MF (Hercules, Wilmington, Del.), lichenan, oat β-glucan (Quaker Oats Co., Barrington, Ill.), barley β-glucan, (Biocon U.S., Inc, Kentucky) laminarin (U.S. Biochem, Cleveland, Ohio), dextran, starch, citrus pectin, maize pectin, polyuronides (Sigma), arabinan, galactan (Koch-Light, Colnbrook, England), arabinogalactan, yeast mannan, and galactomannan (Sigma).

The effect of pH on the enzyme activities was examined using McIlvaine buffers (pH 2.5–8) at 37° C. β-xylanases (A and B) have a broad optimum pH range between pH 4.5–6. The feraxanases (C, D and E) have a pH optimum between pH 6.5 to 7.0.

D. Substrate specificity

Feraxanase preparations (C, D and E) degraded MAX and did not attack Rhodymenia (1→3), (1→4)-β-D-xylan or larch arabino-(1→4)-β-D-xylan. Gel chromatography of the three enzyme digests on a TSK-Gel G 4000 PW column and on Bio Gel P-10 showed that the three feraxanase preparations are endo-type hydrolases and yielded identical fragmentation patterns (FIGS. 4 and 5). Table II shows linkages present in the three fractions which had been separated on the Bio Gel P-10 chromatogram. The major linkages in the smaller fractions (fractions II and III) are terminal arabinofuranosyl, 5-linked-arabinofuranosyl, 4-linked-xylopyranosyl, 3,4-linked-xylopyranosyl and terminal-glucuronosyl residues. Monomers, dimers, trimers or tetramers of xylose and/or arabinose were not detected in the enzyme hydrolyzate of MAX when subjected to HPLC analysis on an Aminex HPX 42A column.

TABLE II

Sugar Linkage Composition of Fractions Obtained by Bio Gel P-10 Chromatography of a Purified Feraxanase (Enzyme Preparation-E) of MAX

| Sugar linkages | | Fractions [a] | | |
|---|---|---|---|---|
| | | I | II | III |
| ara | t | 15.6 | 27.7 | 24.1 |
| | 2 | 2.0 | 1.3 | 1.2 |
| | 3 | 2.0 | 1.1 | 0 |
| | 5 | 4.0 | 5.9 | 12.5 |
| xyl | t | 0.8 | 0.7 | 0 |
| | 4 | 12.0 | 7.5 | 7.1 |
| | 2,4/3,4 | 44.9 | 43.5 | 42.3 |
| gal | t | 4.0 | 0 | 0 |
| | 4 | 3.9 | 0 | 0 |
| UA | total [b] | 7.9 | 11.0 | 12.2 |

[a] Fractions I, II and III obtained from Bio Gel P-10 chromatography (FIG. 5) were concentrated, desalted, lyophilized and subjected to the methylation analysis.
[b] Total uronic acid content was estimated by the Blumenkrantz's procedure.

On the other hand, the β-xylanases (Enzyme preparations A and B) had limited action on MAX even after prolonged incubation (Table III and FIG. 4). However, they degraded Rhodymenia and larch xylans (Table III). Extensive digestion of Rhodymenia xylans by the two β-xylanases gave a fragmentation pattern similar to the pattern obtained by Kato and Nevins, Plant Physiol 75:753–758, supra. One of the β-xylanases appears identical to the β-(1→4)-xylanase previously purified and characterized. Id.

TABLE III

Susceptibility of Xylans With Different Sugar Linkages Arrangements to Purified B. Subtilis Hydrolase Preparations

| | | Plant source of xylans | | |
|---|---|---|---|---|
| Sugar linkages | | Rhodymenia | Larch | Maize |
| | | (Mole %) | | |
| ara | t | 0 | 8.0 | 25.5 |
| | 5 | 0 | 0 | 7.8 |
| Xyl | t | 0.2 | 2.3 | 1.6 |
| | 3 | 21.4 | 0 | 0 |
| | 4 | 67.0 | 69.9 | 14.9 |
| | 2,4/2,3 | 0 | 13.4 | 41.1 |
| gal | t | 0 | 0 | 0.4 |
| | 4 | 0 | 0 | 0.4 |
| glcUA | total | 0 | 2.8 | 8.2 |

| Enzyme preparations [a] | Enzyme activities [b] Reducing sugar formed [c] (μg from 1 mg substrate) | | |
|---|---|---|---|
| A | 87 | 133 | 3 |
| B | 100 | 164 | 4 |
| C | n.d.[d] | n.d. | 22 |
| D | n.d. | n.d. | 24 |
| E | n.d. | n.d. | 25 |

[a] Purified enzyme preparations (0.2 μg each) from Bio Gel P-10 rechromatography were used (See Table I)
[b] Enzyme preparations A and B were incubated with 0.1% solution of individual substrates for 10 min under the conditions described. Preparations C, D and E were incubated for 2 h under the same conditions.
[c] Amounts of reducing groups formed during enzyme reaction were estimated by the procedure of Somogyi and Nelson and expressed as xylose equivalents.
[d] No enzyme activity was detected during prolonged incubation period (24 h).

Dissociation of feraxan from maize coleoptile sections by the enzyme preparations FIG. 6 shows the time course for dissociation of feraxan from the maize coleoptile sections. Addition of 0.2 μg of individual feraxanases (enzyme preparations C, D, and E) liberated ca. 1.7 mg of carbohydrates (xylose equivalents) and ca. 50 μg of phenolic acid (ferulic acid equivalents) from 10 mg of ethanol-boiled coleoptile preparations. On the other hand, β-xylanases (enzyme preparations A and B) (1 μg) liberated less than one tenth the components liberated by feraxanases.

Sugar composition of enzyme digestion products of maize cell wall and the whole dry coleoptile preparation as estimated by 2M TFA hydrolysis and 72% sulfuric acid hydrolysis are shown in Table IV. A feraxanase (enzyme preparation E) liberated more than 70% of arabinose, xylose and ferulic acid present in the coleoptile preparation. Table IV also shows that β-glucanase-pretreatment or pectin-extraction by ammonium oxalateoxalic acid buffer did not decrease the recovery of arabinose, xylose and ferulic acid dissociated by the action of the feraxanase. On the other hand, pretreatment of the coleoptile sections with alkaline solutions removed most of the feraxan from the coleoptile sections, substantially decreasing the recovery of arabinose and xylose from residues.

TABLE IV

Sugar Compositions of Whole Coleoptile Sections and Enzyme Digest of Different Wall Preparations

| | Rha | Fuc | Ara | Xyl | Man | Gal | Glc | UA | FA |
|---|---|---|---|---|---|---|---|---|---|
| Acid-hydrolysates/Base saponification product of whole coleptile | | | | | | | | | |
| Treatment [a] | Amount (μg/mg of original dry coleptile) | | | | | | | | |
| 2M-TFA | 3.8 | 1.4 | 78.5 | 102.2 | 3.9 | 35.0 | 121.3 | — | — |
| 72% Sulfuric acid | 4.8 | 1.8 | 75.1 | 111.8 | 12.3 | 36.6 | 399.8 | 56.5 | — |
| 0.5 M NaOH | — | — | — | — | — | — | — | — | 7.23 |
| Enzyme hydrolysates of differentially pretreated coleoptile preparations | | | | | | | | | |
| Pretreatment [b] / Treatment [c] | Amount (μg/mg of original dry coleoptile) | | | | | | | | |
| Buffer / Buffer | 0 | 0 | 0 | 0 | 0 | 0 | 5.8 | 0 | — |
| Buffer / Feraxanase | 0 | 0 | 75.5 | 79.3 | 0 | 10.1 | 17.1 | 25.3 | 5.51 |
| Buffer / Glucanase | 0 | 0 | 0 | 0 | 0 | 0 | 115.8 | 4.3 | 0 |
| Glucanase / Feraxanase | 0 | 0 | 78.3 | 87.6 | 0 | 17.4 | 5.1 | 24.8 | 5.85 |
| Preextraction [d] | | | | | | | | | |
| AO / Feraxanase | 0 | 0 | 82.5 | 97.7 | 0 | 20.2 | 5.0 | — | — |
| AO + 4% KOH / Feraxanase | 0 | 0 | 16.8 | 19.7 | 0 | 5.2 | 0.6 | — | — |
| AO + 24% KOH / Feraxanase | 0 | 0 | 6.4 | 8.0 | 0 | 1.9 | 0.1 | — | — |

[a] Dry coleoptile sections of maize were hydrolyzed with 2N TFA or 72% sulfuric acid and sugar composition of the hydrolyzate was analyzed. Saponification was performed with 0.5 M NaOH and ferulic acid content was determined by HPLC.
[b] Dry coleoptile sections were pretreated with or without the β-glucanase.
[c] Pretreated or preextracted coleoptile preparations were treated with a purified feraxanase (enzyme preparation E) or the β-glucanase followed by analyses of sugar compositions and ferulic acid in the hydrolyzate.
[d] Dry coleoptile sections were extracted with ammonium oxalate-oxalic acid buffer solution to remove pectin (AO). After that, the residue was extracted with 4% KOH (AO + 4% KOH) or 24% KOH (AO + 24% KOH) solution.

Linkage analysis of maize cell wall fragments liberated by a feraxanase (enzyme preparation E)

Glycosidic linkages found in the enzyme digest are shown in Table V. The mole percentages of the major linkages (t-ara, 5-ara, 4-xyl and 2,4/3,4-xyl) are similar to those found in alkaline extracted polysaccharide MAX (cf. Table II and Table V) except that a higher percentage of 4-linked-xylopranosyl residues is present in the alkaline extracted MAX.

TABLE V

Sugar Linkage Composition of the Fraction Liberated from Maize Coleoptile Sections by the Action of a Purified Feraxanase (Enzyme Preparation E)

| Sugar linkages [a] | | Amount Mole % |
|---|---|---|
| ara | t | 29.2 |
| | 2 | 1.7 |
| | 3 | 1.5 |
| | 5 | 7.0 |
| xyl | t | 1.5 |
| | 4 | 6.4 |
| | 2,4/3,4 | 41.0 |
| gal | t | 1.3 |
| | 4 | 0.3 |
| UA | total | 10.1 |

[a] Feraxanase digestion product derived from maize cell walls were desalted, lyophilized and subjected to the methylation analysis. UA content was estimated by the Blumenklantz's procedure.

Although the present invention has been described in some detail by way of illustration and example for purposes of clarity and understanding, the illustrations and examples should not be construed as a limitation upon the claims.

We claim:

1. A composition comprising a substantially pure enzyme which degrades arabinoxylan and has a molecular weight of about 45,000.

2. The composition of claim 1, wherein said enzyme has a pH optimum between about 6.5 to about 7.0.

3. The composition of claim 2, wherein the enzyme selectively dissociates feraxan from an ethanol treated maize coleoptile preparation.

4. A composition comprising an enzyme having a molecular weight of about 45,000 which degrades arabinoxylan and which is unable to degrade Rhodymenia (1→3), (1→4)-β-D-xylan.

5. The composition of claim 4, wherein said composition is further characterized by having a pH optimum between about 6.5 to about 7.0.

6. The composition of claim 4, wherein said composition further selectively dissociates feraxan from a maize cell wall preparation.

7. The composition of claim 3 or 6, wherein said enzyme is further unable to degrade larch arabino-(1→4)-β-D-xylan.

8. The composition of claim 3 or 6, wherein said composition releases fragments in a maize cell wall preparation comprised of:
   (1) C1 and C5 of arabinofuranosyl;
   (2) C1 of terminal arabinofuranosyl;
   (3) C1 and C4 of xylopyranosyl;
   (4) C2 and C4 of xylopyranosyl or C3 and C4 of xylopyranosyl; and
   (5) C1 of terminal glucuronosyl.

9. The composition of claim 3 or 6, wherein said composition releases 2,4/3,4-linked-xylopyranosyl, terminal-arabinofuranosyl, 5-linked-arabinofuranosyl, 4-linked-xylopyranosyl, terminal-glucurono-pyranosyl and esterified ferulic acid from maize arabinoxylan.

10. A composition of a substantially pure enzyme preparation which degrades arabinoxylan and which has a molecular weight of about 45,000 prepared by purification of said enzyme from Bacillus sp. extracts.

11. A composition of claim 10 wherein the purification comprises a purification step selected from at least one of the following steps: differential precipitation using salts, ion exchange chromatography, molecular filtration, HPLC, ultrafiltration, diafiltration, electrophoresis and isoelectricfocusing.

12. A composition of claim 11 wherein the purification is comprised of a combination of at least two of the purification steps.

* * * * *